US010577340B1

(12) United States Patent
Wei et al.

(10) Patent No.: US 10,577,340 B1
(45) Date of Patent: Mar. 3, 2020

(54) BERAPROST-314D CRYSTALS AND METHODS FOR PREPARATION THEREOF

(71) Applicant: CHIROGATE INTERNATIONAL INC., Yangmei, Taoyuan County (TW)

(72) Inventors: Shih-Yi Wei, Yangmei (TW); Jian-Bang Jheng, Yangmei (TW)

(73) Assignee: CHIROGATE INTERNATIONAL INC., Yangmei (TW)

(*) Notice: Subject to any disclaimer, the term of this patent is extended or adjusted under 35 U.S.C. 154(b) by 0 days.

(21) Appl. No.: 16/199,443

(22) Filed: Nov. 26, 2018

(51) Int. Cl.
*C07D 307/79* (2006.01)

(52) U.S. Cl.
CPC ........ *C07D 307/79* (2013.01); *C07B 2200/13* (2013.01)

(58) Field of Classification Search
CPC .................................................. C07D 307/79
USPC ........................................................ 549/458
See application file for complete search history.

(56) References Cited

U.S. PATENT DOCUMENTS

2014/0275237 A1* 9/2014 Faulds ............... A61K 31/5585
514/468

FOREIGN PATENT DOCUMENTS

| JP | 59134787 | * | 8/1984 | |
|----|----------|---|--------|---|
| KR | 1777632 | * | 9/2017 | |
| WO | WO-2012174407 A1 | * | 12/2012 | ........... C07D 307/93 |
| WO | WO-2017027706 A1 | * | 2/2017 | ........... C07D 307/93 |
| WO | WO-2017174439 A1 | * | 10/2017 | ........... C07D 307/93 |

OTHER PUBLICATIONS

Kobayashi; Beilstein J. Org. Chem. 2015, 11, 2654-2660. (Year: 2015).*
Wakita; Heterocycles 2000, 53, 1085-1110. (Year: 2000).*

* cited by examiner

*Primary Examiner* — Daniel R Carcanague
(74) *Attorney, Agent, or Firm* — Ladas & Parry LLP

(57) ABSTRACT

The present invention provides crystalline Forms II and III of Beraprost-314d, and processes for the preparation thereof.

10 Claims, 5 Drawing Sheets

BERAPROST-314D CRYSTALS AND METHODS FOR PREPARATION THEREOF

FIELD OF THE INVENTION

The present invention relates in general to solid forms of prostacyclin derivatives and in particular, to solid crystalline forms of Beraprost-314d and preparation methods thereof.

BACKGROUND OF THE INVENTION

Beraprost is a synthetic benzoprostacyclin analogue of natural prostacyclin consisting of four isomers (Beraprost-314d, Beraprost-314d's enantiomer, Beraprost-315d and Beraprost-315d's enantiomer), as shown in Scheme A. Among them, optically pure Beraprost-314d (termed as Esuberaprost, APS-314d or BPS-314d) is the pharmacologically active isomer, and is currently under clinical trials as an added-on active pharmaceutical ingredient in the inhaled treprostinil (Tyvaso®) for the treatment of diseases, such as pulmonary arterial hypertension in North America and Europe. The preparation of Beraprost-314d has been previously described, e.g., in *Heterocycles,* 2000, 53, 1085-1092, U.S. Pat. No. 8,779,170, and WO 2017/174439.

Scheme A

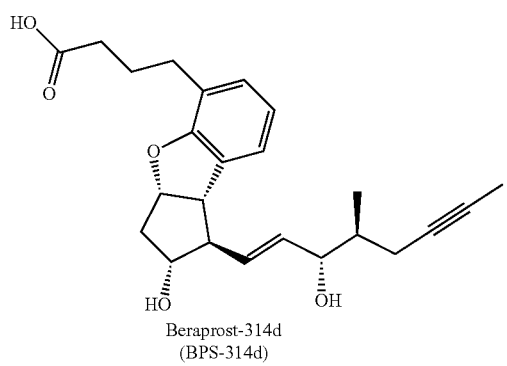

Beraprost-314d
(BPS-314d)

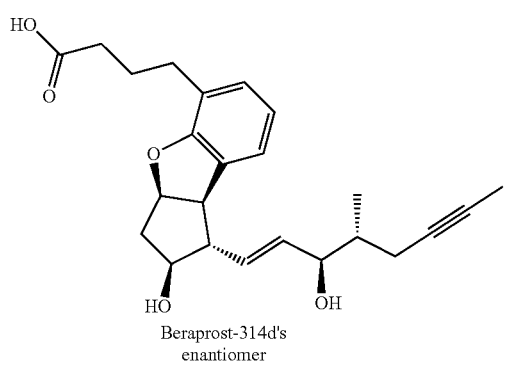

Beraprost-314d's
enantiomer

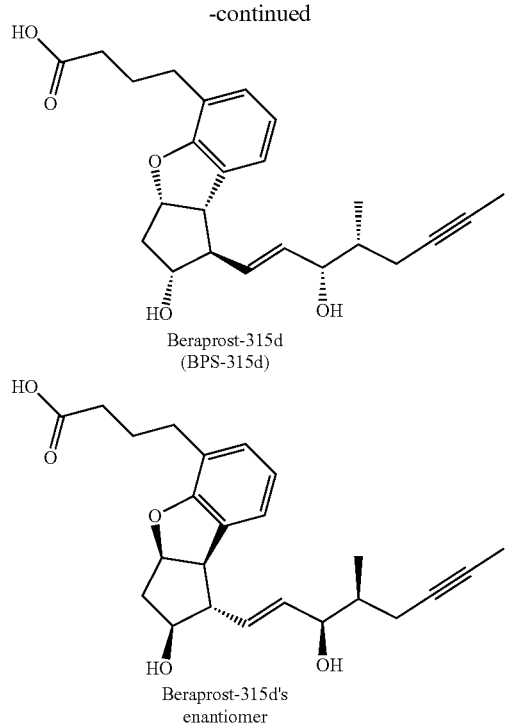

A stable solid form of Beraprost-314d crystal can be widely used in storage, shipment, and handling for commercial considerations. Additionally, a stable Beraprost-314d crystal having fixed physicochemical properties can provide constant operating parameters, e.g., solubility for regular pharmaceutical formulation and steady bioabsorbability for pharmacological treatment. WO 2017/174439 discloses a crystalline form of Beraprost-314d (termed as Form I). However, it does not disclose the stability data of Beraprost-314d crystal Form I, so it is uncertain whether there exists a crystalline form transformation for Beraprost-314d crystal Form I or not. Thus, the benefits of the conventional crystallization methods for preparing a stable Beraprost-314d crystal cannot be evaluated based on the prior art reference.

Consequently, there is a demand for crystallization methods for the preparation of a stable solid form of Beraprost-314d crystal in an efficient and economical way where the novel Beraprost-314d crystal form can remain stable when stored at room temperature for commercial use.

SUMMARY OF THE INVENTION

According to one aspect, the present invention provides a stable solid form of Beraprost-314d crystal Form II, and processes for the preparation thereof.

In one embodiment, the present invention provides a method for preparing a crystalline Form II of Beraprost-314d, which comprises dissolving Beraprost-314d in a first solvent selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, and mixtures thereof to form a homogenous solution; lowering the temperature and/or adding a second solvent selected from the group consisting of pentane, hexane, heptane, octane, nonane, decane, cyclopentane, cyclohexane, cycloheptane, and mixtures thereof to the homogenous solution; and stirring until a precipitate is formed.

In one embodiment, the present invention provides a crystalline Form II of Beraprost-314d having an X-ray powder diffraction (XRPD) pattern exhibiting its five strongest characteristic peaks at the following 2θ reflection angles: 6.1±0.2°, 6.6±0.2°, 7.2±0.2°, 12.1±0.2°, and 16.3±0.2°.

In one embodiment, the present invention provides a crystalline Form II of Beraprost-314d having a differential scanning calorimetry (DSC) thermogram pattern comprising an endothermic peak with a peak onset temperature of approximately 62.2±1° C. and a peak maximum of approximately 67.5±1° C.

According to one aspect, the present invention provides a solid form of Beraprost-314d crystal Form III, and processes for the preparation thereof.

In one embodiment, the present invention provides a method for preparing a crystalline Form III of Beraprost-314d, which comprises dissolving Beraprost-314d in a third solvent selected from the group consisting of ethyl ether, isopropyl ether, methyl tert-butyl ether, ethyl acetate, isopropyl acetate, dichloromethane, and mixtures thereof to form a homogenous solution; lowering the temperature and/or adding a fourth solvent selected from the group consisting of pentane, hexane, heptane, octane, nonane, decane, cyclopentane, cyclohexane, cycloheptane, and mixtures thereof to the homogenous solution; and stirring until a precipitate is formed.

In one embodiment, the present invention provides a crystalline Form III of Beraprost-314d having an XRPD pattern exhibiting its five strongest characteristic peaks at the following 2θ reflection angles: 6.2±0.2°, 7.2±0.2°, 12.4±0.2°, 15.7±0.2°, and 19.3±0.2°.

In one embodiment, the present invention provides a crystalline Form III of Beraprost-314d having a DSC thermogram pattern comprising an endothermic peak with a peak onset temperature of approximately 61.9±1° C. and a peak maximum of approximately 66.2±1° C.

The present invention provides a solid form of Beraprost-314d crystal Form II, which can remain stable when stored at room temperature without crystalline transformation for commercial use. On the other hand, the prepared Beraprost-314d crystal Form III will slowly convert to Form II while keeping at room temperature It is further proved that the solid form of Beraprost-314d crystal Form II is the most stable form of Beraprost-314d.

DETAILED DESCRIPTION OF THE INVENTION

Figure 1:
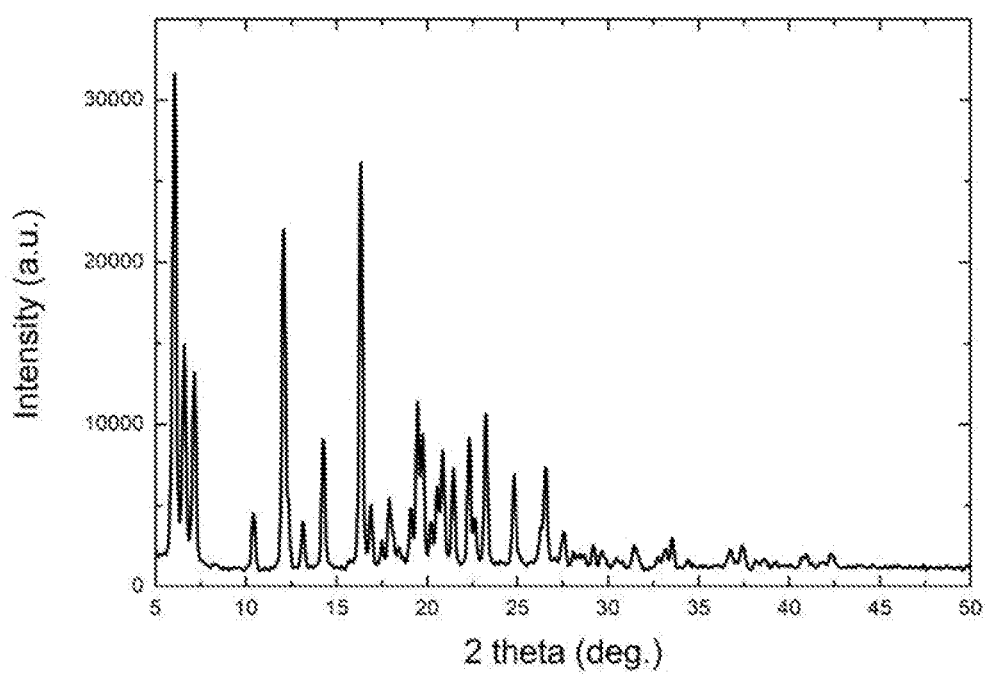
FIG. 1 shows an X-ray powder diffraction (XRPD) pattern of Beraprost-314d crystal Form II.

Beraprost-314d Crystal Form II and Preparation Thereof

In an embodiment of the present invention, the method for preparing Beraprost-314d crystal Form II comprises the steps of:
(a) dissolving crude Beraprost-314d in a first solvent selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, and mixtures thereof to form a homogenous solution;
(b) lowering the temperature and/or adding a second solvent selected from the group consisting of pentane, hexane, heptane, octane, nonane, decane, cyclopentane, cyclohexane, cycloheptane, and mixtures thereof to the homogeneous solution;
(c) stirring until a precipitate is formed:
(d) filtering out the precipitate thereby isolating the Beraprost-314d crystal Form II; and
(e) optionally drying the Beraprost-314d crystal Form II.

The selection of the first solvent is the key to determine whether a Beraprost-314d crystal Form II can be formed. In the present invention, the first solvent used to dissolve the crude Beraprost-314d is selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, and mixtures thereof, preferably ethyl acetate and isopropyl acetate. The volume of the first solvent may be about 0.5 ml to about 100 ml, preferably about 1 ml to about 50 ml, and more preferably about 2 ml to about 25 ml, per 1 g of the crude Beraprost-314d. The crude Beraprost-314d can be dissolved in the first solvent at a temperature ranging from about 0° C. to about 80° C., preferably from about 10° C. to about 70° C., and more preferably from room temperature to about 60° C.

In one embodiment of the present invention, the temperature of the homogenous solution is lowered to a temperature ranging from about −30° C. to about 60° C., preferably from about −20° C. to about 50° C., and more preferably from about −10° C. to about 40° C.

In a preferred embodiment, the volume of the second solvent selected from the group consisting of pentane, hexane, heptane, octane, nonane, decane, cyclopentane, cyclohexane, cycloheptane, and mixtures thereof may be about 0.5 ml to about 20 ml, preferably about 1 ml to about 10 ml, and more preferably about 2 ml to about 5 ml, per 1 ml of the first solvent. The second solvent can be added at a temperature ranging from about −30° C. to about 60° C., preferably from about −20° C. to about 50° C., and more preferably from about −10° C. to about 40° C.

In one embodiment of the present invention, the precipitation of the crystal may be performed at a temperature ranging from about −30° C. to about 60° C., preferably from about −20° C. to about 50° C., and more preferably from about −10° C. to about 40° C.

In one embodiment of the present invention, the step of filtering out the precipitate comprises using the second solvent or a mixture of the first solvent and the second solvent to wash the precipitate. In the mixing solvent, the ratio of the first solvent and the second solvent may be about 1:1 to about 1:100, preferably about 1:2 to about 1:10.

In one embodiment of the present invention, the Beraprost-314d crystal Form II has an X-ray powder diffraction (XRPD) pattern exhibiting its five strongest characteristic peaks at the following 2θ reflection angles: 6.1±0.2°, 6.6±0.2°, 7.2±0.2°, 12.1±0.2°, and 16.3±0.2°. In a preferred embodiment, the XRPD pattern further comprises characteristic peaks at the following 2θ reflection angles: 14.3±0.2°, 19.5±0.2°, 19.7±0.2°, 20.6±0.2°, 20.9±0.2°, 21.4±0.2°, 22.3±0.2°, 23.2±0.2°, 24.8±0.2°, and 26.6±0.2°. More preferably, the XRPD pattern of Beraprost-314d crystal Form II is consistent with FIG. 1. The particular data of Beraprost-314d crystal Form II is shown in Table 1.

TABLE 1

| 2θ angle (°) | d value (Å) | relative intensity (%) |
|---|---|---|
| 6.1 | 14.6 | 100.0 |
| 6.6 | 13.4 | 46.1 |
| 7.2 | 12.4 | 40.9 |
| 10.4 | 8.5 | 12.9 |
| 12.1 | 7.3 | 69.0 |
| 13.1 | 6.7 | 11.1 |
| 14.3 | 6.2 | 27.6 |
| 16.3 | 5.4 | 82.4 |
| 16.9. | 5.2 | 14.5 |
| 17.5 | 5.1 | 7.4 |
| 17.9 | 5.0 | 15.8 |
| 18.4 | 4.8 | 6.0 |
| 19.1 | 4.6 | 13.8 |
| 19.5 | 4.6 | 35.0 |
| 19.7 | 4.5 | 28.5 |
| 20.2 | 4.4 | 1.10 |
| 20.6 | 4.3 | 18.2 |
| 20.9. | 4.3 | 25.4 |
| 21.4. | 4.1 | 21.9 |
| 22.3 | 4.0 | 27.8 |
| 22.6 | 3.9 | 11.9 |
| 23.2 | 3.8 | 32.4 |
| 24.0 | 3.7 | 3.5 |
| 24.8 | 3.6 | 20.6 |
| 26.3 | 3.4 | 10.3 |
| 26.6 | 3.4 | 22.0 |
| 27.1 | 3.3 | 4.1 |
| 27.6 | 3.2 | 9.2 |
| 28.1 | 3.2 | 5.2 |
| 28.4 | 3.1 | 4.8 |
| 28.7 | 3.1 | 4.6 |
| 29.2 | 3.1 | 6.5 |
| 29.6 | 3.0 | 5.4 |
| 30.5 | 2.9 | 4.0 |
| 30.8 | 2.9 | 3.4 |
| 31.5 | 2.8 | 6.6 |
| 32.7 | 2.7 | 4.3 |
| 33.2 | 2.7 | 5.8 |
| 33.5 | 2.7 | 8.0 |
| 34.4 | 2.6 | 3.6 |
| 36.8 | 2.4 | 5.7 |
| 37.4 | 2.4 | 6.5 |
| 38.2 | 2.4 | 3.6 |
| 38.6 | 2.3 | 3.8 |
| 40.7 | 2.2 | 4.2 |
| 41.0 | 2.2 | 4.8 |
| 42.3 | 2.1 | 4.9 |

In one embodiment, the present invention provides a Beraprost-314d crystal Form II having an XRPD pattern substantially as shown in FIG. 1.

Figure 2:
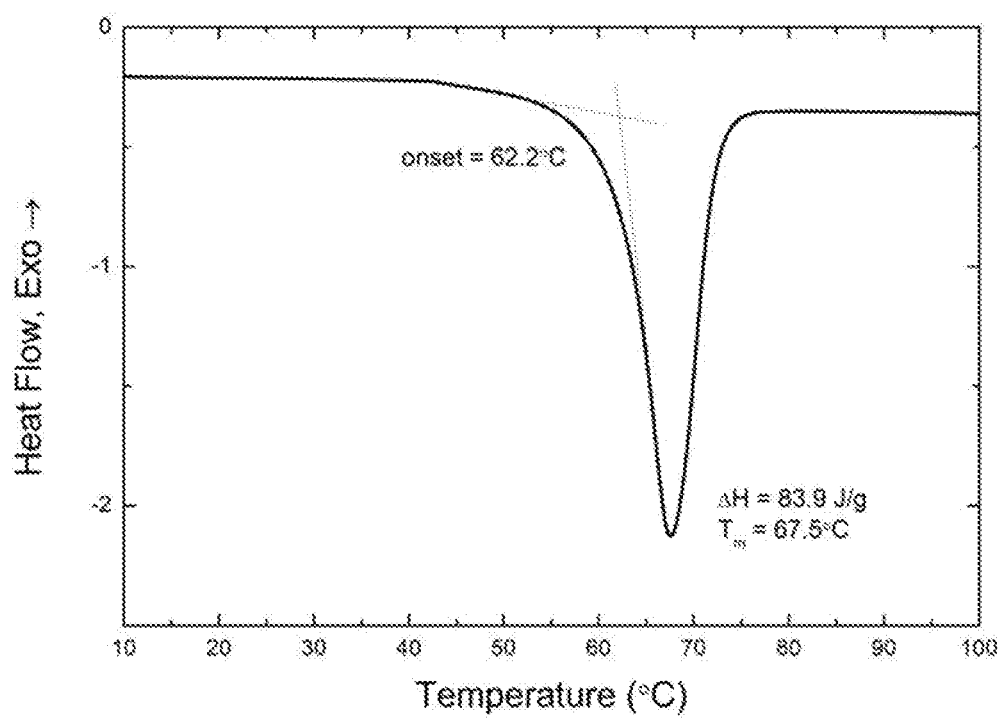
FIG. 2 shows a differential scanning calorimetry (DSC) thermogram pattern of Beraprost-314d crystal Form II.

In one embodiment, the present invention provides a Beraprost-314d crystal Form II having a differential scanning calorimetry (DSC) thermogram pattern comprising an endothermic peak with a peak onset temperature of approximately 62.2±1° C. and a peak maximum of approximately 67.5±1° C. In a preferred embodiment, the present invention provides a Beraprost-314d crystal Form II having a DSC thermogram pattern substantially as shown in FIG. 2.

Due to the organic solvent system used in the method of the present invention, the precipitated Beraprost-314d crystal Form II possesses compact solid characteristics and thus is easy to be filtered out. Moreover, the residual solvents can be easily removed under high vacuum at room temperature.

In addition, Beraprost-314d crystal Form II is a stable crystalline form, which shows good stability, with no other crystalline forms or degraded products of impurities, even after six months of placement under normal storage temperatures (about −20° C.).

Beraprost-314d Crystal Form III and Preparation Thereof

In an embodiment of the present invention, the method for preparing Beraprost-314d crystal Form III comprises the steps of:

(a) dissolving crude Beraprost-314d in a third solvent selected from the group consisting of ethyl ether, isopropyl ether, methyl tert-butyl ether, ethyl acetate, isopropyl acetate, dichloromethane, and mixtures thereof to form a homogenous solution, (b) lowering the temperature and/or adding a fourth solvent selected from the group consisting of pentane, hexane, heptane, octane, nonane, decane, cyclopentane, cyclohexane, cycloheptane, and mixtures thereof to the homogeneous solution;

(c) stirring until a precipitate is formed;

(d) filtering out the precipitate thereby isolating the Beraprost-314d crystal Form III; and (e) optionally drying the Beraprost-314d crystal Form III.

The selection of the third solvent is the key to determine whether a Beraprost-314d crystal Form III can be formed. In the present invention, the third solvent used to dissolve the crude Beraprost-314d is selected from the group consisting of ethyl ether, isopropyl ether, methyl tert-butyl ether, ethyl acetate, isopropyl acetate, dichloromethane, and mixtures thereof, preferably methyl tert-butyl ether and dichloromethane. The volume of the third solvent may be about 0.5 ml to about 100 ml, preferably about 1 ml to about 50 ml, and more preferably about 2 ml to about 25 ml, per 1 g of the crude Beraprost-314d. The crude Beraprost-314d can be dissolved in the third solvent at a temperature ranging from about 0° C. to about 80° C., preferably from about 10° C. to about 70° C., and more preferably from room temperature to about 60° C.

In one embodiment of the present invention, the temperature of the homogenous solution is lowered to a temperature ranging from about 0° C. to about 60° C., preferably from about 10° C. to about 50° C., and more preferably from about 20° C. to about 40° C.

In a preferred embodiment, the volume of the fourth solvent selected from the group consisting of pentane, hexane, heptane, octane, nonane, decane, cyclopentane, cyclohexane, cycloheptane, and mixtures thereof may be about 0.5 ml to about 20 ml, preferably about 1 ml to about 10 ml, and more preferably about 2 ml to about 5 ml, per 1 ml of the third solvent. The fourth solvent can be added at a temperature ranging from about 0° C. to about 60° C., preferably from about 10° C. to about 50° C., and more preferably from about 20° C. to about 40° C.

In one embodiment of the present invention, the precipitation of the crystal may be performed at a temperature ranging from about 0° C. to about 60° C., preferably from about 10° C. to about 50° C., and more preferably from about 20° C. to about 40° C.

In one embodiment of the present invention, the step of filtering out the precipitate comprises using the fourth solvent or a mixture of the third solvent and the fourth solvent to wash the precipitate. In the mixing solvent, the ratio of the third solvent and the fourth solvent may be about 1:1 to about 1:100, preferably about 1:2 to about 1:10.

In one embodiment of the present invention, the Beraprost-314d crystal Form III has an XRPD pattern exhibiting its five strongest characteristic peaks at the following 2θ reflection angles: 6.2±0.2°, 7.2±0.2°, 12.4±0.2°, 15.7±0.2°, and 19.3±0.2°. In a preferred embodiment, the XRPD pattern further comprises characteristic peaks at the following 2θ reflection angles: 11.9±0.2°, 14.3±0.2°, 17.5±0.2°, 17.9±0.2°, 18.7±0.2°, 20.4±0.2°, 21.5±0.2°, 22.6±0.2°, 23.0±0.2°, and 24.8±0.2°. More preferably, the XRPD pattern of Beraprost-314d crystal Form III is consistent with FIG. 3. The particular data of Beraprost-314d crystal Form III is shown in Table 2.

TABLE 2

| 2θ angle (°) | d value (Å) | relative intensity (%) |
|---|---|---|
| 6.2 | 14.2 | 100.0 |
| 7.2 | 12.3 | 49.4 |
| 9.3 | 9.5 | 3.7 |
| 10.2 | 8.7 | 11.8 |
| 11.9 | 7.4 | 18.5 |
| 12.4 | 7.1 | 60.6 |
| 14.3 | 6.2 | 18.1 |
| 15.7 | 5.6 | 45.9 |
| 17.5 | 5.1 | 16.3 |
| 17.9 | 5.0 | 14.7 |
| 18.7 | 4.7 | 24.9 |
| 19.3 | 4.6 | 41.2 |
| 20.4 | 4.4 | 19.4 |
| 21.5 | 4.1 | 15.1 |
| 22.6 | 3.9 | 18.9 |
| 23.0 | 3.9 | 19.0 |
| 23.7 | 3.8 | 5.6 |
| 24.1 | 3.7 | 5.4 |
| 24.8 | 3.6 | 14.4 |
| 27.1 | 3.3 | 11.2 |
| 27.9 | 3.2 | 6.0 |
| 28.8 | 3.1 | 3.9 |
| 30.4 | 2.9 | 4.5 |
| 31.6 | 2.8 | 5.1 |
| 34.1 | 2.6 | 4.0 |
| 35.8 | 2.5 | 3.9 |
| 36.2 | 2.5 | 5.3 |
| 37.8 | 2.4 | 5.1 |
| 39.0 | 2.3 | 3.3 |

Figure 3:
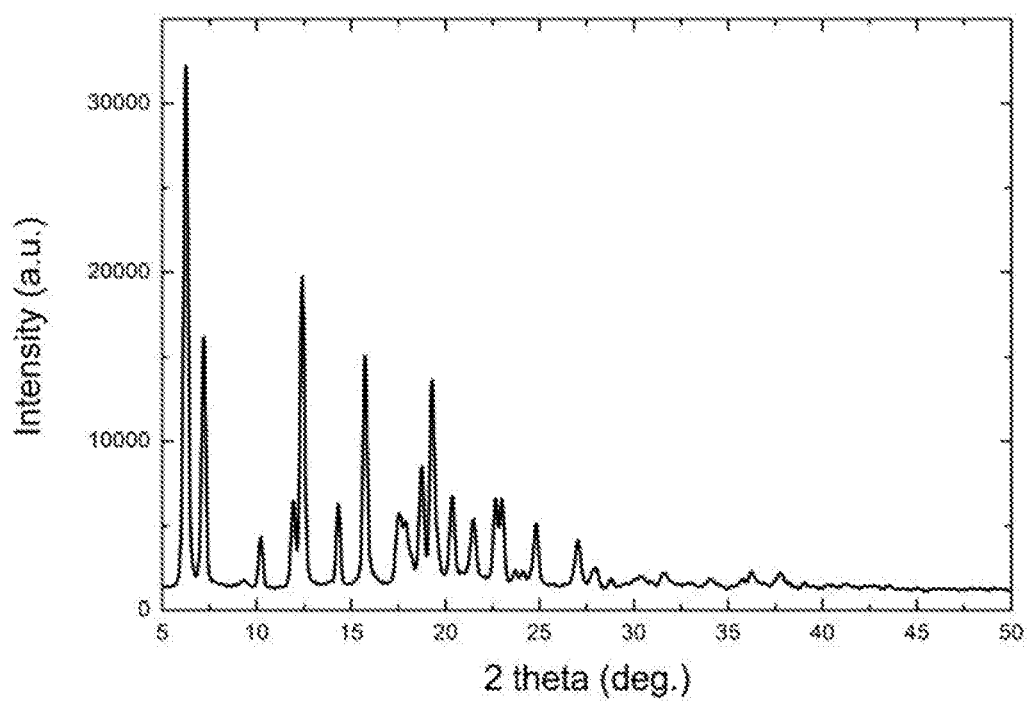
FIG. 3 shows an XRPD pattern of Beraprost-314d crystal Form III.

In one embodiment, the present invention provides a Beraprost-314d crystal Form III having an XRPD pattern substantially as shown in FIG. 3.

Figure 4:
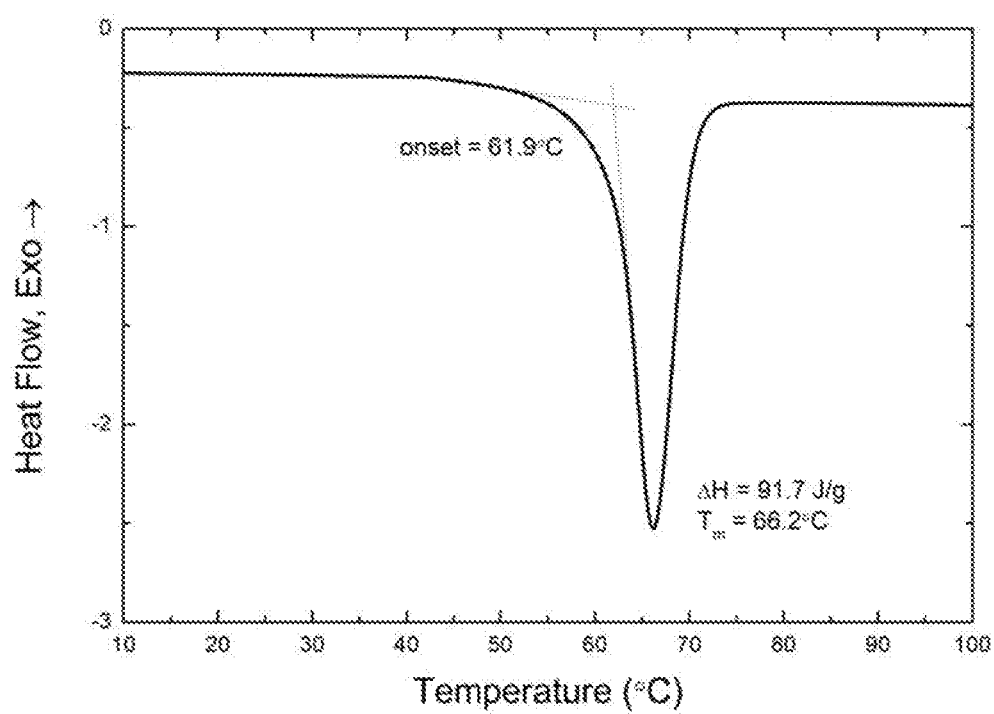
FIG. 4 shows a DSC thermogram pattern of Beraprost-314d crystal Form III.

In one embodiment, the present invention provides a Beraprost-314d crystal Form III having a DSC thermogram pattern comprising an endothermic peak with a peak onset temperature of approximately 61.9±1° C. and a peak maximum of approximately 66.2±1° C. In a preferred embodiment, the present invention provides a Beraprost-314d crystal Form III having a DSC thermogram pattern substantially as shown in FIG. 4.

Stability of Beraprost-314d Crystal Form II

For applications in therapeutic fields, the most stable crystalline form at room temperature, which has steady physicochemical properties, is preferred and usually selected for use in pharmaceutical formulations and treatment.

In one embodiment, the Beraprost-314d crystal Form II is a stable crystalline form, which shows good stability with no other crystalline forms during storage under normal storage temperatures (about −20° C.) for six months.

In one embodiment, the Beraprost-314d crystal Form II is a stable crystalline form, which shows good stability with no other crystalline forms during storage at room temperature (about 20 to 25° C.) for six months.

Figure 5:
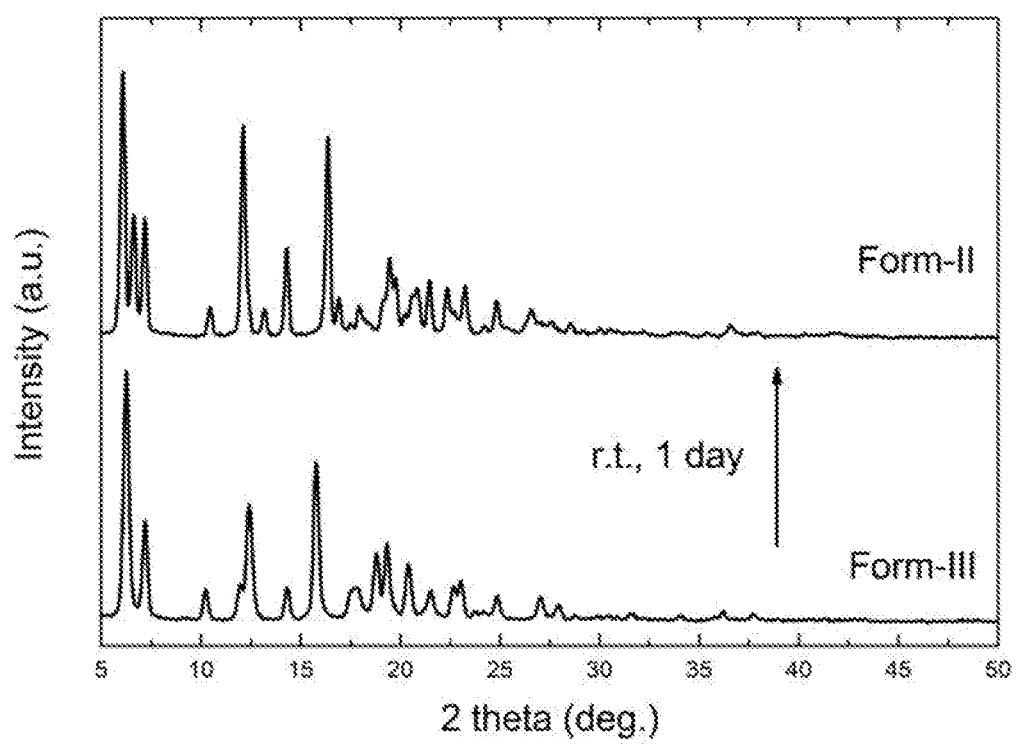
FIG. 5 shows the crystalline form transformation from Beraprost-314d crystal Form III to Form II at room temperature for 1 day.

In one embodiment, the Beraprost-314d crystal Form III is not a stable crystalline form at room temperature. The Beraprost-314d crystal Form III will be converted to Beraprost-314d crystal Form II while keeping at room temperature for 1 day at most, as shown in FIG. 5. This result indicates that the Beraprost-314d crystal Form II is the most stable crystalline form at room temperature.

Therefore, the Beraprost-314d crystal Form II is the most stable crystalline form at room temperature without crystalline form transformation, which can provide steady physicochemical properties for pharmaceutical formulations, and is advantageous in that it can be widely and safely used in storage, shipment, and handling for commercial considerations.

EXAMPLES

X-ray Powder Diffraction (XRPD) Analysis: The XRPD patterns were collected on a Bruker D2 PHASER diffractometer with fixed divergence slits and ID LYNXEYE detector. The samples (ca. 100 mg) were flatly placed on a sample holder. The prepared samples were analyzed over a 2θ range from 5° to 50° with step size of 0.02 degrees and step time of 1 second using $CuK_\alpha$ radiation at a power of 10 mA and 30 kV. The $CuK_\beta$ radiation was removed by a divergent beam nickel filter.

Differential Scanning Calorimetry (DSC) Analysis: The DSC thermogram patterns were collected on a TA DISCOVERY DSC 25 instrument. The samples (ca. 5 mg) were weighed into an aluminum pan with a crimping closed aluminum lid. The prepared samples were analyzed from 10° C. to 100° C. at a scan rate of 10° C./min under a flow of nitrogen (ca. 50 ml/min). The melting temperature and heat of fusion were calibrated by indium (In) before measurement.

Example 1

Preparation of Crude Beraprost-3144

2,3,3a,8b-Tetrahydro-2-hydroxy-1-(3-hydroxy-4-methyl-1-octen-6-ynyl)-1H-cyclopenta[b]benzofuran-5-butanoic acid methyl ester (50.0 g, 121.2 mmol) was dissolved in 200 ml methanol and followed by addition of 200 ml IN sodium hydroxide/water solution and stirred for 2 hours. The reaction mixture was isolated by acid-base extraction, and the solvent was evaporated off under vacuum. The crude product was purified by chromatography on silica gel using a mixture of hexane and ethyl acetate as a gradient eluent to obtain 33.2 g crude Beraprost-314d.

Example 2

Preparation of Beraprost-314d Crystal Form II

Crude Beraprost-314d (1.00 g, from Example 1) and ethyl acetate (10 ml) were heated to 40° C. for dissolution and then cooled to room temperature. N-hexane (20 ml) was added slowly dropwise and the mixture was stirred in ice water bath for 18 hours until solid precipitation occurred. Afterwards, the resulting suspension was filtered and rinsed, and then dried under high vacuum at room temperature for 24 hours to give 0.75 g Beraprost-314d crystal Form II. The XRPD and DSC results are the same as shown in FIG. 1 and FIG. 2.

Example 3

Preparation of Beraprost-314d Crystal Form II

Crude Beraprost-314d (1.00 g from Example 1) and isopropyl acetate (20 ml) were heated to 40° C. for dissolution and then cooled to room temperature. N-heptane (40 ml) was added slowly dropwise and the mixture was stirred in ice water bath for 22 hours until solid precipitation occurred. Afterwards, the resulting suspension was filtered and rinsed, and then dried under high vacuum at room temperature for 24 hours to give 0.73 g Beraprost-314d crystal Form II. The XRPD and DSC results are the same as shown in FIG. 1 and FIG. 2.

Example 4

Preparation of Beraprost-314d Crystal Form II

Crude Beraprost-314d (0.50 g, from Example 1) and acetone (7.5 ml) were heated to 40° C. for dissolution and then cooled to room temperature. N-pentane (15 ml) was added slowly dropwise and the mixture was stirred in ice water bath for 20 hours until solid precipitation occurred. Afterwards, the resulting suspension was filtered and rinsed, and then dried under high vacuum at room temperature for 24 hours to give 0.36 g Beraprost-314d crystal Form II. The XRPD and DSC results are the same as shown in FIG. 1 and FIG. 2.

Example 5

Preparation of Beraprost-314d Crystal Form III

Crude Beraprost-314d (1.00 g, from Example 1) and methyl tert-butyl ether (15 ml) were heated to 40° C. for dissolution and then cooled to room temperature. N-hexane (30 ml) was added slowly dropwise and the mixture was stirred at room temperature for 18 hours until solid precipitation occurred. Afterwards, the resulting suspension was filtered and rinsed, and then dried under high vacuum at room temperature for 24 hours to give 0.74 g Beraprost-314d crystal Form III. The XRPD and DSC results are the same as shown in FIG. 3 and FIG. 4.

Example 6

Preparation of Beraprost-314d Crystal Form III

Crude Beraprost-3144 (0.5 g, from Example 1) and methyl tert-butyl ether (10 ml) were heated to 40° C. for dissolution and then cooled to room temperature. N-heptane (20 ml) was added slowly dropwise and the mixture was stirred at room temperature for 20 hours until solid precipitation occurred. Afterwards, the resulting suspension was filtered and rinsed, and then dried under high vacuum at room temperature for 24 hours to give 0.37 g Beraprost-314d crystal Form III. The XRPD and DSC results are the same as shown in FIG. 3 and FIG. 4.

Example 7

Preparation of Beraprost-314d Crystal Form III

Crude Beraprost-314d (0.5 g, from Example 1) and dichloromethane (10 ml) were heated to 40° C. for dissolution and then cooled to room temperature. N-pentane (20 ml) was added slowly dropwise and the mixture was stirred at room temperature for 20 hours until solid precipitation occurred. Afterwards, the resulting suspension was filtered and rinsed, and then dried under high vacuum at room temperature for 24 hours to give 0.35 g Beraprost-314d crystal Form III. The XRPD and DSC results are the same as shown in FIG. 3 and FIG. 4.

Example 8

Crystalline Form Transformation from Beraprost-314d Crystal Form III to Form II

The Beraprost-314d crystal Form III (0.5 g, from Example 5) was placed in a glass vial, and isothermal at room temperature for 1 day. Afterwards, the Beraprost-314d crystal Form III was completely converted to Beraprost-314d crystal Form II, as shown in FIG. 5.

What is claimed is:

1. A crystalline Form II of Beraprost-314d, characterized by having an X-ray powder diffraction (XRPD) pattern comprising its five strongest characteristic peaks at the following 2θ reflection angles: 6.1±0.2°, 6.6±0.2°, 7.2±0.2°, 12.1±0.2°, and 16.3±0.2°.

2. The crystalline Form II of Beraprost-314d of claim 1, wherein the XRPD pattern further comprises characteristic peaks at the following 2θ reflection angles: 14.3±0.2°, 19.5±0.2°, 19.7±0.2°, 20.6±0.2°, 20.9±0.2°, 21.4±0.2°, 22.3±0.2°, 23.2±0.2°, 24.8±0.2°, and 26.6±0.2°.

3. The crystalline Form II of Beraprost-314d of claim 1, wherein the XRPD pattern is substantially shown in FIG. 1.

4. The crystalline Form II of Beraprost-314d of claim 1, further having a differential scanning calorimetry (DSC) thermogram pattern comprising an endothermic peak with a peak onset temperature of approximately 62.2±1° C. and a peak maximum of approximately 67.5±1° C.

5. The crystalline Form II of Beraprost-314d of claim 4, wherein the DSC thermogram pattern is substantially shown in FIG. 2.

6. A crystalline Form III of Beraprost-314d, characterized by having an X-ray powder diffraction (XRPD) pattern comprising its five strongest characteristic peaks at the following 2θ reflection angles: 6.2±0.2°, 7.2±0.2°, 12.4±0.2°, 15.7±0.2°, and 19.3±0.2°.

7. The crystalline Form III of Beraprost-314d of claim 6, wherein the XRPD pattern further comprises characteristic peaks at the following 2θ reflection angles: 11.9±0.2°, 14.3±0.2°, 17.5±0.2°, 17.9±0.2°, 18.7±0.2°, 20.4±0.2°, 21.5±0.2°, 22.6±0.2°, 23.0±0.2°, and 24.8±0.2°.

8. The crystalline Form III of Beraprost-314d of claim 6, wherein the XRPD pattern is substantially shown in FIG. 3.

9. The crystalline Form III of Beraprost-314d of claim 6, further comprising a differential scanning calorimetry (DSC) thermogram pattern comprising an endothermic peak with a peak onset temperature of approximately 61.9±1° C. and peak maximum of approximately 66.2±1° C.

10. The crystalline Form III of Beraprost-314d of claim 9, wherein the DSC thermogram pattern is substantially shown in FIG. 4.

* * * * *